(12) United States Patent
Adnan

(10) Patent No.: US 7,080,557 B2
(45) Date of Patent: Jul. 25, 2006

(54) METHOD AND APPARATUS FOR INSPECTING A TUBULAR USING ACOUSTIC SIGNALS

(75) Inventor: Sarmad Adnan, Sugar Land, TX (US)

(73) Assignee: Schlumberger Technology Corp., Sugar Land, TX (US)

( * ) Notice: Subject to any disclaimer, the term of this patent is extended or adjusted under 35 U.S.C. 154(b) by 44 days.

(21) Appl. No.: 10/820,082

(22) Filed: Apr. 7, 2004

(65) Prior Publication Data

US 2004/0200282 A1 Oct. 14, 2004

Related U.S. Application Data

(60) Provisional application No. 60/461,114, filed on Apr. 8, 2003.

(51) Int. Cl.
*G01N 29/28* (2006.01)
(52) U.S. Cl. .......................... 73/622; 73/644
(58) Field of Classification Search ................. 73/622, 73/644
See application file for complete search history.

(56) References Cited

U.S. PATENT DOCUMENTS

| | | | |
|---|---|---|---|
| 3,583,211 A * | 6/1971 | Brech et al. ................ | 73/623 |
| 4,019,373 A | 4/1977 | Freeman et al. ............ | 73/71.5 |
| 4,055,990 A | 11/1977 | Topping ..................... | 73/623 |
| 4,166,395 A * | 9/1979 | Dannehl ..................... | 73/634 |
| 4,202,216 A | 5/1980 | Bull et al. ................... | 73/639 |
| 4,486,025 A | 12/1984 | Johnston .................... | 277/31 |
| 4,718,277 A | 1/1988 | Glascock ..................... | 73/622 |
| 5,303,592 A | 4/1994 | Livingston | |
| 5,600,069 A | 2/1997 | Girndt et al. | |
| 5,826,654 A | 10/1998 | Adnan et al. | |
| 6,321,596 B1 | 11/2001 | Newman | |
| 6,443,242 B1 | 9/2002 | Newman et al. | |
| 6,527,056 B1 | 3/2003 | Newman | |
| 6,578,422 B1 | 6/2003 | Lam et al. | |
| 6,782,751 B1 * | 8/2004 | Linares et al. .............. | 73/622 |

FOREIGN PATENT DOCUMENTS

| | | |
|---|---|---|
| GB | 2 109 555 | 6/1983 |
| WO | 2004/025291 | 3/2004 |
| WO | WO 2004/025291 | 3/2004 |

OTHER PUBLICATIONS

J. Krautkramer et al., Ultrasonic Testing of Materials, 3$^{rd}$ Ed., Springer-Verlag, New York, 1983, pp. 439-445.*

* cited by examiner

*Primary Examiner*—John E. Chapman
(74) *Attorney, Agent, or Firm*—Robin Nava; Tim Curington

(57) ABSTRACT

A method and apparatus for acoustically inspecting a tubular member is presented. In particular a method for inspecting coiled tubing using ultrasound is presented. The method includes contacting a tubular with a coupling material, transmitting an acoustic signal, receiving a returned acoustic signal and then releasing the contact of the coupling material with the tubular. The method has particular application for determining the wall thickness of coiled tubing as it is being unreeled into a borehole or wound on coiled tubing reel.

17 Claims, 2 Drawing Sheets

METHOD AND APPARATUS FOR INSPECTING A TUBULAR USING ACOUSTIC SIGNALS

CROSS-REFERENCE TO OTHER APPLICATIONS

This application claims priority on U.S. provisional application No. 60/461,114 entitled "Method for improved ultrasonic coupling" and filed Apr. 8, 2003, incorporated herein in its entirety by reference.

BACKGROUND OF THE INVENTION

1. Field of the Invention

The present invention relates to a method for inspecting a tubular, and more particularly relates to a method for inspecting coiled tubing using ultrasound.

2. Related art

Coiled tubing is pipe stored on a reel known to be useful for a variety of applications. In particular, coiled tubing is useful for being run into and pulled out of a bore, tubular string, borehole, pipeline, well or wellbore to accomplish desired operations. In use, the coiled tubing is unwound from the coiled tubing reel and fed or injected into a borehole. After completing a downhole use or operation, the coiled tubing is withdrawn from the borehole and rewound on the reel. The repeated bending caused by unwinding and rewinding the coiled tubing can degrade or damage the coiled tubing. Other factors, such as the pressures to which the coiled tubing is subjected, the number of times the coiled tubing is run into and pulled out of the borehole, and the type and configuration of equipment used to deploy and retrieve the coiled tubing from the borehole, also stress the coiled tubing in a variety of ways that can degrade or damage it. This damage, called fatigue damage, can cause the coiled tubing to weaken and ultimately fail. Fatigue damage limits the useful life of coiled tubing. Coiled tubing parameters that may indicate fatigue damage are monitored to confirm that coiled tubing remains in suitable and safe condition for use in a given job environment. Monitoring of parameters such as number of cycles of use; radii of bending, forces applied to the coiled tubing; length, diameter, and wall thickness of the coiled tubing; material properties; and internal pressures is useful in predicting the useful life of coiled tubing. In particular, monitoring of the wall thickness of the coiled tubing is important as it can be affected by corrosive or erosive fluids or slurries pumped through it as well as fatigue stresses.

One method known for measuring or monitoring parameters of tubulars is ultrasonic testing. For example, U.S. Pat. No. 5,600,069, incorporated herein by reference, presents an ultrasonic assembly and method of testing useful for measuring tubing parameters as a manufacturing quality confirmation test. Methods of ultrasonic testing more particularly adapted for detecting inner surface flaws near the ends of tubulars and across welds are described in U.S. Pat. No. 6,578,422, incorporated herein by reference.

Ultrasonic testing devices for coiled tubing are known. U.S. Pat. No. 5,303,592 incorporated herein in its entirety by reference, describes an ultrasonic apparatus and methods of use for inspecting coiled tubing wherein coiled tubing is passed through a cylindrical test apparatus coupled to the coiled tubing while ultrasonic signals are transmitted into and returned from the coiled tubing. The success of ultrasonic testing of coiled tubing depends on the ability to transmit a signal from the ultrasound transducers to the coiled tubing. Water may be used to provide coupling between the ultrasonic transducers and the coiled tubing as described in U.S. Pat No. 5,303,592. However, other fluids and debris in a borehole environment can contaminate and dirty water, which interferes with its ability to relay the signals transmitted from the ultrasonic transducers and returned from the coiled tubing.

Another approach such as described in WO 2004/025291 involves an apparatus and method of transmitting and receiving ultrasonic signals to and from the coiled tubing through an elastomeric element coupled with the tubing. The elastomeric element material may be cylindrical, surrounding the coiled tubing around its circumference, over a certain axial length. Ultrasonic transducers, capable of transmitting and receiving acoustic signals, are placed around the elastomeric element, generally along its exterior circumference. The elastomeric element, transducers, and other mechanisms may be provided in a housing. Such a housing may also provide a means to mount or locate the apparatus near the injector device during operational use.

The quality of the ultrasonic signal provided to and returned from the coiled tubing greatly depends on the coupling between the elastomeric element and the coiled tubing. While it is desirable that the elastomeric element be firmly pressed against the coiled tubing for optimal signal quality, firm contact of the element with the coiled tubing generates friction as the coiled tubing moves through the apparatus. Such friction can generate heat that can negatively affect the properties of the elastomeric material as well as the coiled tubing. Furthermore, in the scope of the overall operation of deploying and retrieving coiled tubing from a borehole, it is also desirable that minimal constrictions be placed on the coiled tubing to avoid unnecessary friction as it is moved in and out of the borehole to avoid slowing down the job site operations.

It is suggested in WO 2004/025291 to provide a fluid such as oil between the elastomeric material and the coiled tubing to improve sonic coupling. In addition to the disadvantages of using water for coupling, use of other fluids or chemical may simply not be permitted for use in sensitive environments. When a fluid becomes dirty during borehole use, quality of the received signals can be affected. In addition, while use of a lubricant may reduce the friction created by the contact of the elastomeric element with the moving coiled tubing for a certain period of time, as operations proceed, the lubricant will be worn away or degrade under borehole conditions, leading to eventual friction buildup. Finally, it is not clear how the presence and acceptable condition of such a lubricating and coupling fluid would be confirmed during operational use, other than by measuring a frictional induced increase in temperature or drag, that friction itself being indicative of a reduction in the lubricating performance of the fluid.

It is desirable to necessary to accomplish the acoustic coupling between ultrasound transmitters and the coiled tubing that is required for signal quality in such a manner that minimizes friction on the coiled tubing as it is moved in and out of a bore. Further, as it is important from both safety and operational efficiency that the coiled tubing parameters be accurately determined to permit appropriate monitoring of the tubing condition, the method of acquiring such parameter data must be reliable and confirmable. There exists a need for a measurement process that is reliable and confirmable during operational use. Furthermore, there exists a need for a method and apparatus that provides good quality signal transmission for measuring tubing parameters while avoiding or minimizing creating friction during the measurement.

SUMMARY OF THE INVENTION

The present invention provides a method for inspecting a tubular comprising the steps of contacting the tubular with a coupling material, transmitting an acoustic signal, receiving a returned acoustic signal; and releasing the contact of the coupling material with the tubular. In particular embodiments, the acoustic signal may be an ultrasonic signal, the tubular may be a coiled tubing, and/or the coupling material may be an elastomeric element.

In certain embodiments, the steps of contacting, transmitting, receiving, and releasing are repeated along a length of coiled tubing. The method of the present invention may be performed as coiled tubing is being unreeled from a coiled tubing reel and run into a borehole; or being pulled out of a borehole and reeled on a coiled tubing reel. In some embodiments, control algorithms may be used to confirm a returned signal is received or to control operation of the measurement apparatus. In further embodiments, the contact pressure of the coupling material on the tubular may be selectively increased or decreased based on the received signal.

The present invention also comprises an apparatus for use in inspecting tubulars comprising a housing including a coupling material having an axial bore through which a coiled tubing may be passed; an acoustic transducer; an activation cavity; a port; and a solenoid activated hydraulic valve operational to permit or restrict fluid flow in the activation cavity, wherein the hydraulic valve is operational in response to a signal received by the acoustic transducer. In particular embodiments, increasing fluid in the activation chamber in response to a signal received by the acoustic transducer compresses the coupling material to contact the coiled tubing. A hydraulic valve that may be opened or closed at a high rate of speed may be provided. In some embodiments the hydraulic valve is operational in response to a returned signal from the coiled tubing received by the acoustic transducer.

DETAILED DESCRIPTION

Figure 1:
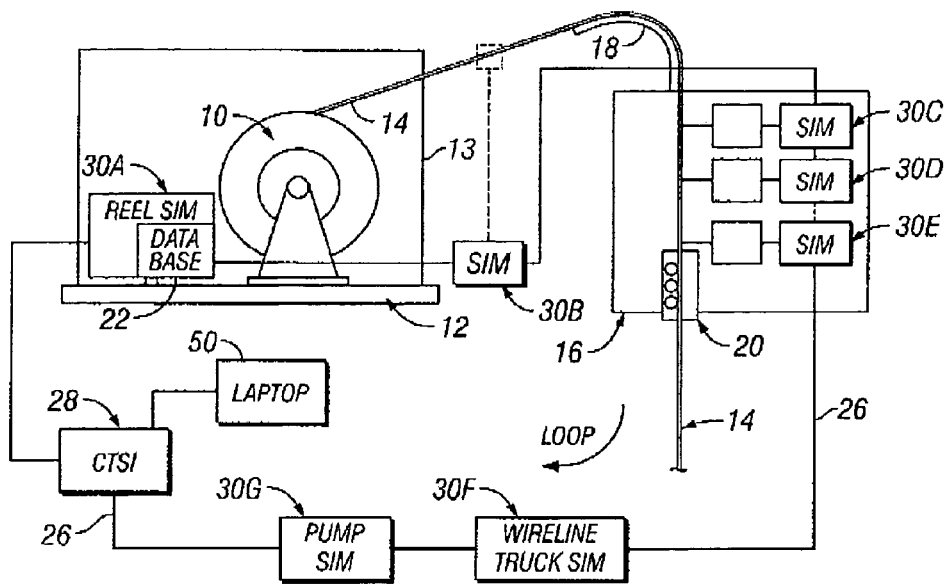
FIG. 1 is a diagrammatic view of a prior art coiled tubing system showing a typical coiled tubing configuration and a system for measuring, recording and storing data which are characteristic of coiled tubing.

Referring to FIG. 1, a known coiled tubing system is shown as disclosed in U.S. Pat. No. 5,826,654, incorporated herein fully by reference. A coiled tubing reel is shown at 10 mounted on a skid 12 for transport from one job site to another job site. Alternatively the coiled tubing reel may be mounted on a truck or trailer. A reel frame 13 on a skid 12 mounts reel 10 for rotation. Coiled tubing shown at 14 is unreeled from the reel 10 for being injected downhole or "run-in-hole" (RIH) and wound onto reel 10 when extracted from the borehole or "pulling-out-of-hole" (POOH). Coiled tubing 14 is used for many downhole applications. A wellhead injection device is shown generally at 16 has a gooseneck 18 for diverting the coiled tubing 14 vertically downwardly. Wellhead injection device 16 includes a drive mechanism for forcing tubing 14 downwardly. A lower wellhead structure 20 receives tubing 14 and may include a blowout preventor (BOP) stack.

Skid 12 with reel frame 13 and reel 10 thereon may be transported from one job site to another. A reel database 22 is permanently mounted on frame 13 for coiled tubing 10 prior to use at its first job site. The reel database 22, fixed on the frame, travels with reel 10 for the entire life of coiled tubing 10. Database 22 includes a memory unit where information concerning coiled tubing 12 is stored for retrieval at each job site. A continuous coiled tubing loop generally indicated at 26 originates at a Coiled Tubing Sensor Interface (CTSI) 28 which forms the main data processing unit at a job site and is looped about and between the equipment or various elements of the system for termination back at CTSI 28.

Figure 2:
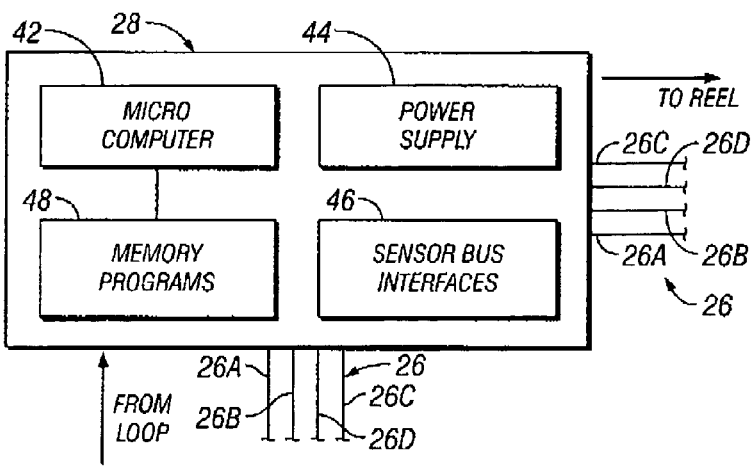
FIG. 2 is a diagrammatic view of a typical sensor interface module provided for each selected characteristic of the coiled tubing to be sensed and positioned in the coiled tubing system.

The CTSI 28 is shown diagrammatically in FIG. 2 including a microcomputer 42, a power supply 44, sensor bus interfaces 26 and a memory that includes a data processing program. Looped cable 26 comprises four shielded wires 26A, 26B, 26C and 26D. Wires 26A and 26B provide power; wires 26C and 26D distribute data to and from various Sensor Interface Modules (SIMs) 30A, 30B, 30C, 30D, 30E, 30F, and 30G located along the continuous cable loop 26 of the CTSI 28 thereby permitting automatic update and maintenance of reel database 22. A Sensor Interface Module (SIM) is normally provided for monitoring each of the selected characteristics or features of the coiled tubing. The SIMs are capable of receiving and/or sending data concerning the selected characteristics or features.

Figure 3:
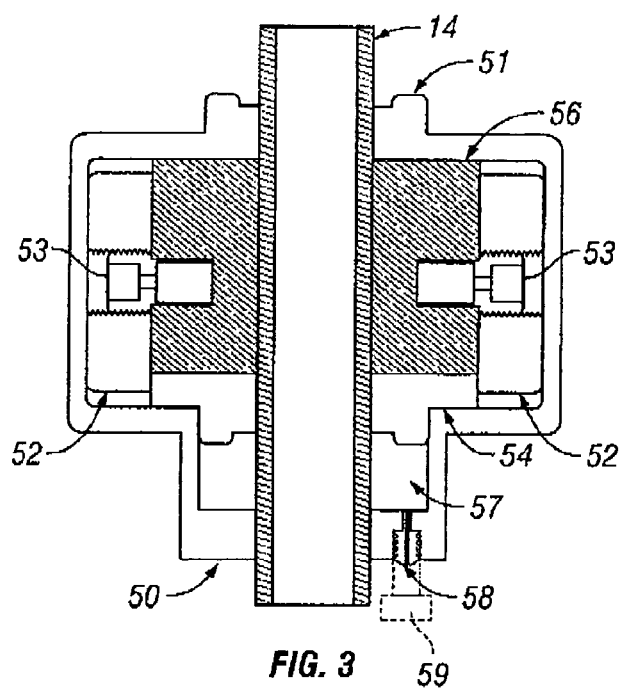
FIG. 3 is an example of a measurement apparatus suitable for use in the method of the present invention.
Figure 4:
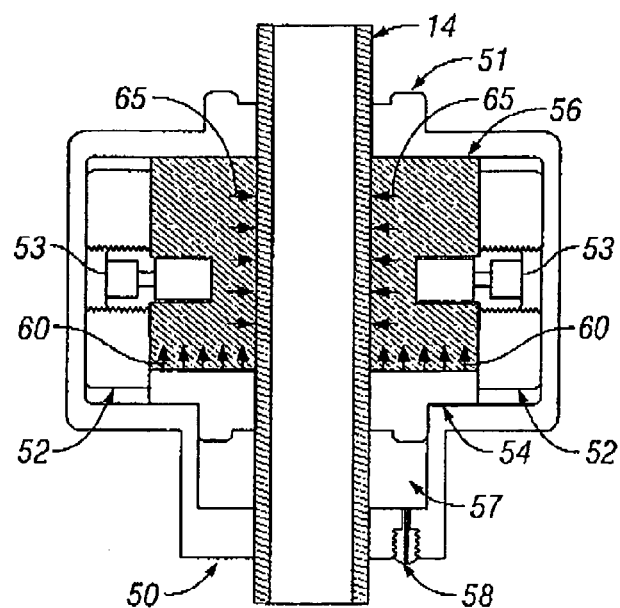
FIG. 4 is the measurement apparatus of FIG. 3 shown under compression.

Referring to FIG 3. a measurement apparatus 50 is shown that comprises a coupling material 56 shown as an elastomeric element in a cavity 57 in a housing 51. Alternative coupling materials include fluids, bladders or other compliant material capable of transmitting an acoustic signal. Typically housing 51 and coupling material 56 may by cylindrical or torroidal in shape. A tubular, such as coiled tubing 14, passes through an axial bore in housing 51 and coupling material 56. Securing mechanisms 52 adjacent to ultrasonic transducers or probes 53 restrict the probes 53 from movement in the radial direction relative the coiled tubing 14 but permit movement in the axial direction. In the embodiment illustrated, two ultrasonic transducers or probes are shown, although the invention is applicable with a single or any number of transducers or probes. Piston 54 may be used to compress (as shown at 60) coupling material element 56 as shown in FIG. 4 in the axial direction of the coiled tubing 14 thereby increasing contact pressure 65 at the coupling material/coiled tubing interface. Piston 54 may be hydraulic or pneumatically operated with fluid or gas being provided to activation cavity 57 via input port 58. Alternatively a solenoid operated hydraulic valve 59 (shown in dashed line) may be used to permit fluid or gas to enter activation cavity 57 via port 58 to compress coupling material 56. If the contact pressure at the coupling material/coiled tubing interface is too great, then normal force on the coiled tubing at the coupling material/coiled tubing interface may translate into extra frictional drag and may cause measurement apparatus 50 grab onto the coiled tubing. In this situation, decreasing the compression force placed axially on the elastomeric element by the piston will decrease the contact pressure at the elastomeric element/coiled tubing interface. If the contact pressure at the coupling material/coiled tubing interface is too low, then the acoustic coupling necessary for transmission of a signal from transducer 53 to coiled tubing 14 would not be achieved. Thus a method is needed that permits acoustic coupling while avoiding frictional drag.

The present invention provides a method of inspecting a tubular comprising contacting a tubular with a coupling material, transmitting a signal, receiving a returned signal and releasing the contact of the coupling material with the tubular. Referring to FIGS. 3 and 4 to illustrate this method, coiled tubing 14 moving through the measurement apparatus 50 is shown. Piston 54, in response to a signal, compresses elastomeric element 56 to contact coiled tubing 14. Ultrasonic transducer 53 transmits an acoustic signal that travels through elastomeric element 56 and into coiled tubing 14. Reflected acoustic signals are returned and received by transducer 53. Then contact of elastomeric element 56 is released from the coiled tubing 14 by reducing or removing the compression asserted on elastomeric element 56 by piston 54. It should be noted that coiled tubing 14 continues to move uniformly through the measurement apparatus 50 as the contact is made, signal transmitted, signal received and contact released. Coupling material 56 flexes and deforms to accommodate the discontinuous relative motion of the coiled tubing 14 through the measurement apparatus 50. This method provides the advantage of accomplishing acoustic coupling between the transducer and coiled tubing while avoiding the friction generated by continuous contact of an elastomeric element with the coiled tubing as it is moved through a measurement apparatus. Additional advantages include a much smaller drag in the coiled tubing, increase wear life for coupling material, and no need for a lubrication fluid between coupling material and coiled tubing.

In further embodiments, this method may be repeated as the coiled tubing 14 moves through the measurement apparatus 50 to provide measurements along the coiled tubing at various locations, In some embodiments, the steps of contacting the coiled tubing with a coupling material, transmitting a signal, receiving a signal and releasing contact of the coiled tubing by the coupling material may be repeated at a high rate (10–100 Hz). In this manner, frequent ultrasonic measurements may made to determine coiled tubing parameters without generating the frictional drag created by continuous contact of an elastomeric element with the coiled tubing.

In operations, coiled tubing 14 is passed through measurement apparatus 50. Each transducer transmits its acoustic signal at specified time intervals at a specified repetition rate for a specified time duration controlled by its associated instrumentation. In some embodiments, the signal is transmitted so frequently (e.g. 50 GHz) that it essentially provides a continuous signal.

The signal transmitted by an ultrasonic transducer 53 passes through the elastomeric element 56 into coiled tubing 14 and is reflected from the inner surface of the coiled tubing back towards the transducer 53. The ultrasonic transducer receives the reflected signal and generates an electrical output signal. The electrical signal output by transducer 53 from a received ultrasonic signal will have several sections. The initial portion of the output signal contains repeated reflections from interfaces within the ultrasonic transducer itself The next section of the output signal contains a reflection from the transducer/elastomeric element interface. Following this would be the section of signal containing the first reflection from the elastomeric element/coiled tubing interface. The next section of signal contains the repeated reflection "ringing" of the reflected signals between the inner and outer walls of the coiled tubing. This "ringing" section of signal is of particular relevance in determining the shape, outer diameter and wall thickness. In addition when determining the wall thickness. the portion of the signal generated from the elastomeric element/coiled tubing interface is of interest. Electronic time correction windows or "gates" on the transducers' operation may be optionally used to restrict the collection and processing of signal information to a specified time window.

The radial thickness of the coupling material 56 between the ultrasonic transducer 53 and the coupling material/coiled tubing interface is determinable from the physical dimensions of the measurement apparatus. Similarly the speed of acoustic transmission in the elastomeric element is a material property that is determinable. Although temperature changes can affect this material property, in the method of the present invention, heat is not generated by frictional contact of the coupling material with the coiled tubing 14 as it moves through measurement apparatus 50. Thus, the expected travel time of the reflected signal from the elastomeric element/coiled tubing interface can be determined.

According to the method of the present invention, a loss of reflected signal can indicate that the ultrasonic signal was not transmitted into the coiled tubing as a result of poor coupling at the elastomeric element/coiled tubing interface. A control algorithm, typically embodied in software, can be used to monitor the reflected signal. In the event of a loss of signal, the software can trigger further compression of the elastomeric material, thereby increasing the contact pressure of the elastomeric material on the coiled tubing at the elastomeric/coiled tubing interface. In another embodiment, a control algorithm can be used to monitor hydraulic actuation pressure drops (e.g. due to leakage or temperature change) to activate the hydraulic valve or open the solenoid activated hydraulic valve to increase and maintain pressure on the elastomeric element to a level sufficient to achieve good coupling between the elastomeric element and the coiled tubing.

In a further embodiment, a control algorithm, typically embodied in software, is used which uses the ultrasonic signal information as an indicator to monitor the frictional drag that acts on the coiled tubing. In response to a loss or significant reduction in received ultrasonic signal, the control algorithm can trigger the solenoid operated hydraulic valve to open further to produce greater contact pressure on the coiled tubing. In response to a significant increase in frictional drag, the control algorithm can trigger the solenoid operated hydraulic valve to close further to produce lesser contact pressure on the coiled tubing. Monitoring of frictional drag can be done by monitoring coiled tubing parameters such as injector motor pressure, injector head running weight, or coiled tubing reel back tension measured and recorded in the SIMs or memory as shown in FIG. 2.

The expected travel time of the reflected signal from the elastomeric element/coiled tubing interface may be useful in setting a first gate to preclude signals from the initial sections of the output signal. A control algorithm, typically embedded in software, can be used to set a first gate to ignore the initial signals received and a second gate at the first large signal after the first gate, the second gate corresponding to the reflection from the elastomeric material/coiled tubing interface. This signal may be used to confirm the distance from the ultrasonic transducer to the outer surface of the coiled tubing by multiplying the speed of sound in the elastomer by the signal time. This distance can be output and stored in an electronic format, such as a computer memory.

To determine the wall thickness of the coiled tubing, the received signal may be processed to determine the time between reflections from the inner and outer surfaces of the coiled tubing. The time period between peaks of the ringing represents the time needed for the ultrasonic signal to travel from the inner surface to the outer surface and back to the inner surface of the coiled tubing. Note that only reflections from the inner surface of the coiled tubing are received at the transducer as the reflection of the signal from the outer surface of the coiled tubing is reflected in a direction away from the transducer. The calculated wall thickness of the coiled tubing at a particular location along its length may then be stored a memory or SIMs as shown in FIG. 2 with such coiled tubing parameter data from being feed back to the CTSI or other coiled tubing parameter measuring and monitoring system.

Generally coiled tubing is inspected during insertion into a wellbore and upon withdrawal from the wellbore, as well as during manufacturing. In operation, the measurement apparatus may typically be positioned adjacent to levelwind that guides the coiled tubing onto and off of the reel. Placement of the measurement apparatus adjacent to the levelwind offers the advantages of being away from the well, being easily accessible for installation and removal, and possibly providing an early indication of tubing fault when running into the well.

In an embodiment of the present invention, a method of monitoring whether excess friction is being generated by contact of the measurement apparatus 50 with the coiled tubing 14 is provided and relieving that excess friction is provided. One indication of the movement of coiled tubing into and out of the wellbore can be measured by the movement of the injector head 16 as an indication of the rate of injection. Another indication of the movement of the coiled tubing can be measured by the sensing the rotation of the coiled tubing reel 10 as an indication of the rate of unspooling. A discrepancy between these two measurements would indicate excessive contact pressure on the coiled tubing creating friction that is slowing coiled tubing between the reel and the injector.

In an alternative embodiment, a method of the present invention is applicable to use with stripper packing elements in use with coiled tubing. When a measurement apparatus such as shown in FIG. 3 is disposed near a stripper element, continuous contact of elastomeric element 56 may create friction on the coiled tubing sufficient to apply a snubbing force to the coiled tubing, resulting in buckling of the tubing. In the case of a stripper element, the contact pressure of the coupling material with the coiled tubing can be maintained at a level sufficient to provide packing of the coiled tubing in the borehole to provide a seal while minimizing the drag placed on the coiled tubing by the stripper element as the coiled tubing is moved through the packer element. An ultrasonic transducer or transducers may be used to transmit a signal through the coupling material to the coiled tubing. The signal may be compared to an expected signal or to previously acquired signals to monitor for a significant increase or decrease in signal. If a significant increase is noted, contact of the coupling material with the coiled tubing may be relaxed. If a significant decrease is noted, the contact pressure of the coupling material with the coiled tubing may be increased. The expected signal may be determined by considering the difference between the static (hanging in well) and dynamic (moving in or out of well) friction of the coiled tubing.

It is seen that the present invention and the embodiments disclosed herein and those covered by the appended claims are well adapted to carry out the objectives and obtain the ends set forth. Certain changes can be made in the subject matter without departing from the spirit and scope of this invention. It is realized that changes are possible within the scope of this invention and it is further intended that each element or step recited in any of the following claims is to be understood as referring to all equivalent elements or steps.

What is claimed is:

1. A method for inspecting a tubular comprising the steps of
   a) contacting the tubular with an elastomeric coupling material;
   b) transmitting an acoustic signal;
   c) receiving a returned acoustic signal;
   d) releasing the contact of the coupling material with the tubular; and
   e) repeating steps a through d along a length of the tubular at a high rate of speed.

2. The method as claimed in claim 1, wherein the acoustic signal is an ultrasonic signal.

3. The method as claimed in claim 1, wherein the tubular is coiled tubing.

4. The method as claimed in claim 3, wherein steps a through d are repeated as the coiled tubing is being reeled on or unreeled from a coiled tubing reel.

5. The method as claimed in claim 1, wherein an algorithm is used to confirm a returned acoustic signal is received.

6. A method for inspecting a tubular comprising the steps of
   contacting the tubular with a coupling material
   transmitting an acoustic signal
   receiving an acoustic returned signal; and
   selectively increasing or decreasing the contact pressure of the coupling material on the tubular based on the received signal.

7. The method as claimed in claim 6, wherein the acoustic signal is an ultrasonic signal.

8. The method as claimed in claim 6, wherein the tubular is coiled tubing.

9. The method as claimed in claim 6, wherein the coupling material comprises an elastomeric element.

10. The method as claimed in claim 9, wherein the selectively increasing the contact pressure is achieved by compressing the elastomeric element.

11. The method as claimed in claim 9, wherein the selectively decreasing the contact pressure is achieved by decreasing hydraulic pressure upon the elastomeric element.

12. The method of claim 6, further comprising comparing the returned signal to an expected signal, wherein the selectively increasing or decreasing the contact pressure is performed based on the comparison of the returned signal to the expected signal.

13. The method of 6, further comprising contacting, transmitting, receiving and selectively increasing or decreasing as the coiled tubing is being run in or pulled out of a borehole.

14. An apparatus for use in inspecting a tubular comprising:
- a housing comprising a coupling material having an axial bore through which a coiled tubing may be passed;
- an acoustic transducer;
- an activation cavity;
- a port;
- a solenoid activated hydraulic valve operational to permit or restrict fluid flow in the activation cavity, and
- means for controlling the hydraulic valve in response to a signal received by the acoustic transducer.

15. An apparatus as claimed in claim 14 wherein increasing fluid in the activation chamber in response to a signal received by the acoustic transducer compresses the coupling material to contact the coiled tubing.

16. An apparatus as claimed in claim 14, wherein the hydraulic valve may be opened and closed at a high rate of speed.

17. An apparatus as claimed in claim 14 wherein the hydraulic valve is operational in response to a signal returned from the coiled tubing and received by the acoustic transducer.

* * * * *